United States Patent
Ludviksson et al.

(10) Patent No.: US 6,806,949 B2
(45) Date of Patent: Oct. 19, 2004

(54) MONITORING MATERIAL BUILDUP ON SYSTEM COMPONENTS BY OPTICAL EMISSION

(75) Inventors: Audunn Ludviksson, Scottsdale, AZ (US); Eric J. Strang, Chandler, AZ (US)

(73) Assignee: Tokyo Electron Limited, Tokyo (JP)

( * ) Notice: Subject to any disclaimer, the term of this patent is extended or adjusted under 35 U.S.C. 154(b) by 123 days.

(21) Appl. No.: 10/331,349

(22) Filed: Dec. 31, 2002

(65) Prior Publication Data

US 2004/0125359 A1 Jul. 1, 2004

(51) Int. Cl.[7] .............................................. G01N 21/00
(52) U.S. Cl. ...................... 356/72; 356/316; 356/632; 118/713; 427/9; 250/458.1
(58) Field of Search ........................ 356/72–73, 311, 356/316, 632; 250/458.1–459.1; 116/202; 118/712–713; 156/345.24–345.25; 427/9; 438/9

(56) References Cited

U.S. PATENT DOCUMENTS

| | | | | |
|---|---|---|---|---|
| 5,712,702 A | * | 1/1998 | McGahay et al. | 356/311 |
| 5,798,016 A | * | 8/1998 | Oehrlein et al. | 156/345.37 |
| 5,947,053 A | * | 9/1999 | Burnham et al. | 116/208 |
| 6,077,387 A | | 6/2000 | Tesauro | |
| 6,124,927 A | * | 9/2000 | Zhong et al. | 356/311 |
| 6,153,123 A | | 11/2000 | Hampden-Smith et al. | |
| 6,750,977 B2 | * | 6/2004 | Otsubo et al. | 356/632 |
| 2002/0089677 A1 | * | 7/2002 | Ziegler et al. | 427/9 |
| 2003/0157242 A1 | * | 8/2003 | Nakano et al. | 427/8 |
| 2003/0185966 A1 | * | 10/2003 | Kim et al. | 118/712 |

* cited by examiner

Primary Examiner—F. L. Evans
Assistant Examiner—Kara Geisel
(74) Attorney, Agent, or Firm—Oblon, Spivak, McClelland, Maier & Neustadt, P.C.

(57) ABSTRACT

A method and system are provided for monitoring material buildup on system components in a plasma processing system. The system components contain emitters that are capable of producing characteristic fluorescent light emission when exposed to a plasma. The method utilizes optical emission to monitor fluorescent light emission from the emitters for determining system component status. The method can evaluate material buildup on system components in a plasma, by monitoring fluorescent light emission from the emitters. Consumable system components that can be monitored using the method include rings, shields, electrodes, baffles, and liners.

47 Claims, 10 Drawing Sheets

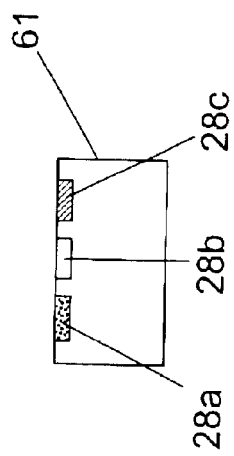
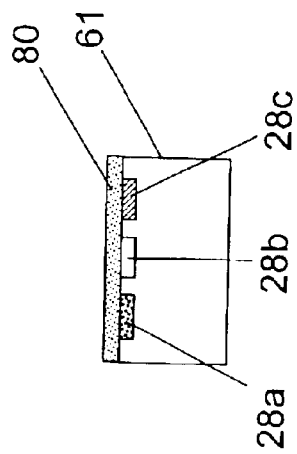
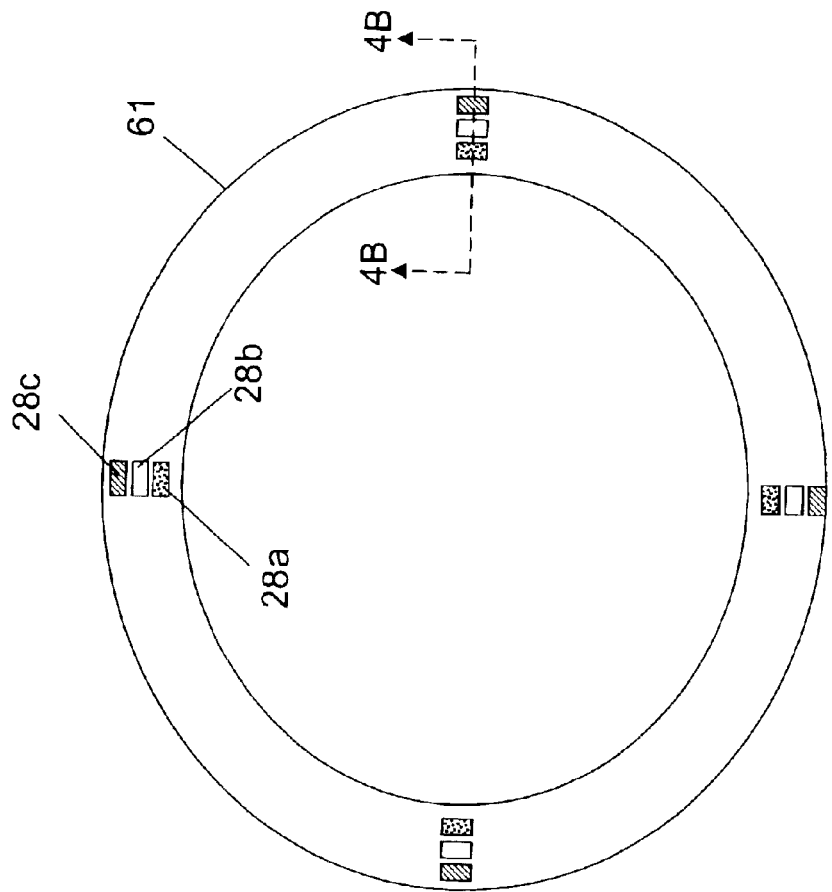

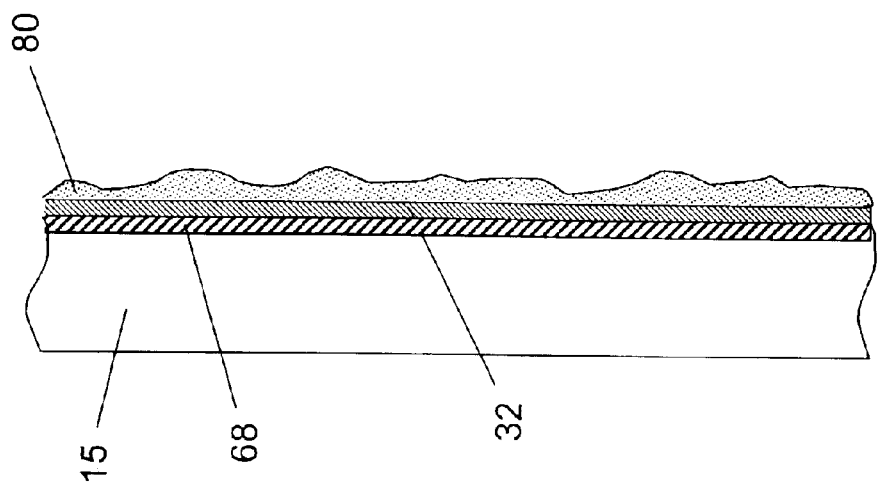
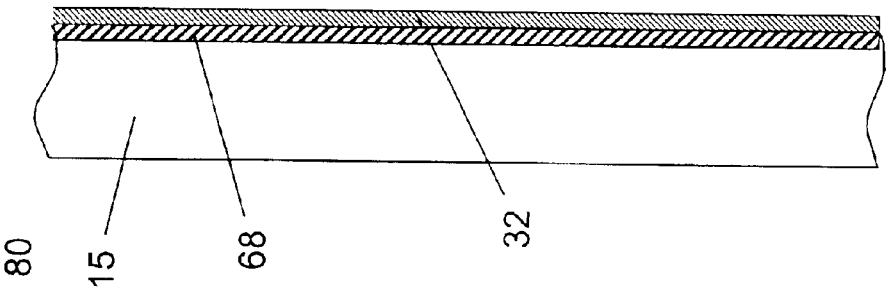
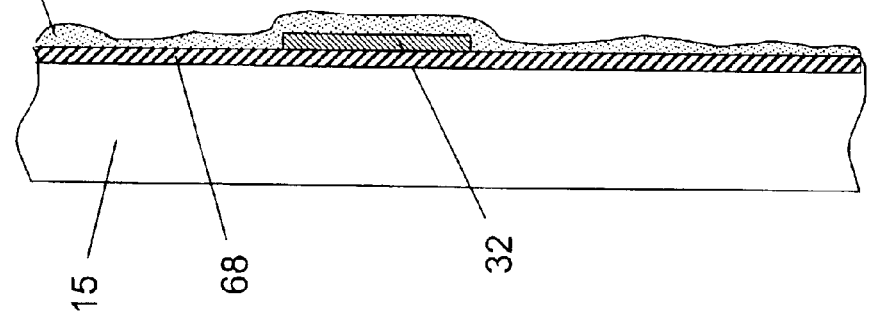
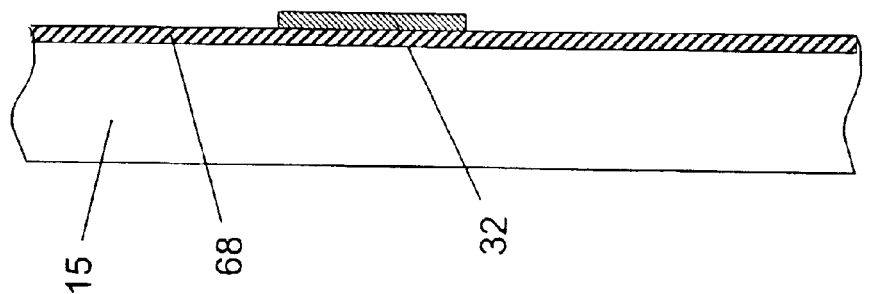

MONITORING MATERIAL BUILDUP ON SYSTEM COMPONENTS BY OPTICAL EMISSION

CROSS REFERENCE TO RELATED APPLICATIONS

The present invention is related to U.S. patent application Ser. No. 10,331,456 file date Dec. 31, 2002, filed on even date herewith, the entire contents of which are herein incorporated by reference.

FIELD OF THE INVENTION

The present invention relates to plasma processing and more particularly to monitoring material buildup on system components in a plasma processing system using an optical monitoring system.

BACKGROUND OF THE INVENTION

The fabrication of integrated circuits (IC) in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions and, therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

Although the formation of a population of charged species (ions, etc.) and chemically reactive species is necessary for performing the function of the plasma processing system (i.e. material etch, material deposition, etc.) at the substrate surface, other component surfaces on the interior of the processing chamber are exposed to the physically and chemically active plasma and, in time, can erode or become coated with deposits. The erosion or coating of exposed system components in the plasma processing system can lead to a gradual degradation of the plasma processing performance and ultimately to complete failure of the system.

Various parts of a plasma processing system consist of consumable or replaceable components that are fabricated from silicon, quartz, alumina, carbon, or silicon carbide, for example. Examples of consumable system components include electrodes, shields, rings, baffles, and liners. The consumable nature of the replaceable components can require frequent maintenance of the plasma processing system. This frequent maintenance can produce costs associated with plasma processing down-time and new plasma processing chamber components, which can be excessive.

Consumable parts are commonly cleaned or replaced after detrimental processing conditions or processing results are observed. These adverse processing conditions can include plasma arcing, particle formation, variations in substrate etch rate, etch selectivity, and etch uniformity. Alternatively, consumable parts can be cleaned or replaced according to a predetermined maintenance schedule that can, for example, be based on the number of plasma operating hours. These methods can result in overdue or premature replacement of consumable system components.

SUMMARY OF THE INVENTION

A plasma processing system is provided that allows for monitoring material buildup on system components during plasma processing. The plasma processing system comprises a processing chamber and an optical monitoring system for monitoring light emission from the processing chamber. System components are provided that can contain at least one emitter that is capable of fluorescent light emission when exposed to a plasma.

A method is provided for monitoring material buildup on system components in a plasma processing system. The system components can contain at least one emitter that can produce characteristic fluorescent light emission when exposed to a plasma. The method utilizes an optical monitoring system to monitor the fluorescent light emission.

Monitorable consumable system components are provided that can contain at least one emitter that can produce characteristic fluorescent light emission when exposed to a plasma. The emitters allow for monitoring material buildup on the consumable system components.

BRIEF DESCRIPTION OF THE DRAWINGS

The accompanying drawings, which are incorporated in and constitute a part of the specification, embodiments of the invention, and together with the general description given above and the detailed description of the embodiments given below, serve to explain the principles of the invention wherein:

FIG. 4A shows a plan view of a system component containing a plurality of emitters;

FIG. 4B shows a cross-sectional view of the system component in FIG. 4A;

FIG. 4C shows a cross-sectional view of the system component in FIG. 4A with a layer of deposited material;

FIG. 9A shows a cross-sectional view of a system component containing an emitter and a protective layer;

FIG. 9B shows a cross-sectional view of the system component in FIG. 9A with a layer of deposited material;

FIG. 10A shows a cross-sectional view of a system component containing an emitter and a protective layer;

FIG. 10B shows a cross-sectional view of the system component in FIG. 10A with a layer of deposited material.

DETAILED DESCRIPTION OF THE INVENTION

Figure 1:
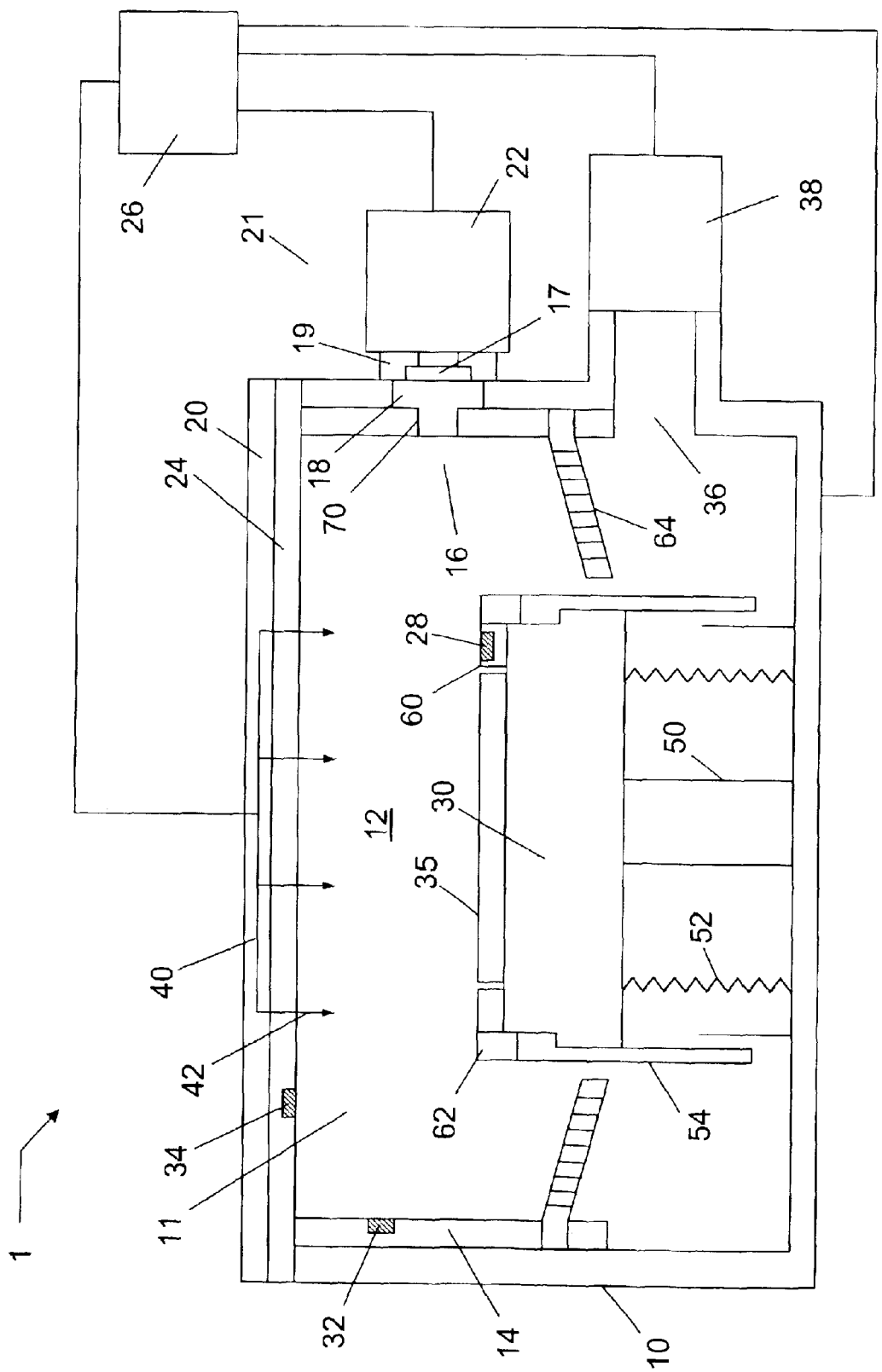
FIG. 1 shows a simplified block diagram of a plasma processing system.

FIG. 1 shows a simplified block diagram of a plasma processing system. A plasma processing system 1 is depicted in FIG. 1 comprising a plasma processing chamber 10, an upper assembly 20, an electrode plate 24, a substrate holder 30 for supporting a substrate 35, and a pumping duct 36 coupled to a vacuum pump 38 for providing a reduced pressure atmosphere 11 in plasma processing chamber 10. Plasma processing chamber 10 can facilitate the formation of a processing plasma in a process space 12 adjacent substrate 35. The plasma processing system 1 can be configured to process various substrates (i.e. 200 mm substrates, 300 mm substrates, or larger).

A gas injection assembly 40 can introduce process gas 42 to the plasma processing chamber 10. The gas injection system 40 can include a showerhead, wherein the process gas 42 is supplied from a gas delivery system (not shown) to the process space 12 through a gas injection plenum (not shown), a series of baffle plates (not shown) and a multi-orifice showerhead gas injection plate (not shown).

For example, an electrode plate 24 can be coupled to an RF source (not shown), and facilitate an upper electrode for the plasma processing system 1. In an alternate embodiment, the upper assembly 20 comprises a cover and an electrode plate 24, wherein the electrode plate 24 is maintained at an electrical potential equivalent to that of the plasma processing chamber 10. For example, the plasma processing chamber 10, the upper assembly 20, and the electrode plate 24 can be electrically connected to ground potential, and facilitate an upper electrode for the plasma processing system 1.

Plasma processing chamber 10 can, for example, further comprise a shield 14 and chamber liners (not shown) for protecting the plasma processing chamber 10 from the processing plasma in the process space 12, and an optical viewport 16. Optical viewport 16 can comprise an optical window 17 coupled to the backside of an optical window deposition shield 18, and an optical window flange 19 can be configured to couple optical window 17 to the optical window deposition shield 18. Sealing members, such as O-rings, can be provided between the optical window flange 19 and the optical window 17, between the optical window 17 and the optical window deposition shield 18, and between the optical window deposition shield 18 and the plasma processing chamber 10. Optical window deposition shield 18 can extend through an opening 70 within shield 14. Optical monitoring system 21 can permit monitoring of optical emission from the processing plasma in process space 12 using optical viewport 16 and optical diagnostic sensor 22.

A spectrometer (not shown) can be incorporated in the optical diagnostic sensor 22 to detect a plasma process condition based on an optical emission, e.g., light, from the process space 12. The spectrometer or the detector system can be associated with a photomultiplier tube, a CCD or other solid state detector to at least partially detect a plasma process condition, such as an endpoint of a plasma process, or material buildup on a system component, for example. However, other optical devices capable of analyzing optical emission, can be used as well.

Substrate holder 30 can, for example, further comprise a vertical translational device 50 surrounded by a bellows 52 coupled to the substrate holder 30 and the plasma processing chamber 10, and configured to seal the vertical translational device 50 from the reduced pressure atmosphere 11 in plasma processing chamber 10. Additionally, a bellows shield 54 can, for example, be coupled to the substrate holder 30 and configured to protect the bellows 52 from the processing plasma. Substrate holder 30 can, for example, further be coupled to at least one of a focus ring 60, and a shield ring 62. Furthermore, a baffle plate 64 can extend about a periphery of the substrate holder 30.

Substrate 35 can be transferred into and out of plasma processing chamber 10 through a slot valve (not shown) and chamber feed-through (not shown) via robotic substrate transfer system where it is received by substrate lift pins (not shown) housed within substrate holder 30 and mechanically translated by devices housed therein. Once substrate 35 is received from substrate transfer system, it is lowered to an upper surface of substrate holder 30.

Substrate 35 can be affixed to the substrate holder 30 via an electrostatic clamping system. Furthermore, substrate holder 30 can, for example, further include a cooling system including a re-circulating coolant flow that receives heat from substrate holder 30 and transfers heat to a heat exchanger system (not shown), or when heating, transfers heat from the heat exchanger system. Moreover, gas can, for example, be delivered to the backside of substrate 35 via a backside gas system to improve the gas-gap thermal conductance between substrate 35 and substrate holder 30. Such a system can be utilized when temperature control of the substrate is required at elevated or reduced temperatures. In other embodiments, heating elements, such as resistive heating elements, or thermoelectric heaters/coolers can be included.

In FIG. 1, substrate holder 30 can comprise an electrode through which RF power is coupled to the processing plasma in process space 12. For example, substrate holder 30 can be electrically biased at a RF voltage via the transmission of RF power from a RF generator (not shown) through an impedance match network (not shown) to substrate holder 30. The RF bias can serve to heat electrons to form and maintain plasma. In this configuration, the system can operate as a reactive ion etch (RIE) reactor, wherein the chamber and upper gas injection electrode serve as ground surfaces. A typical frequency for the RF bias can range from 1 MHz to 100 MHz. For example, plasma processing systems operating at 13.56 MHz are well known to those skilled in the art.

The processing plasma formed in process space 12 can be formed using a plasma source configured to create a plasma from a process. The plasma source can include a parallel-plate, capacitively coupled plasma (CCP) source, an inductively coupled plasma (ICP) source, any combination thereof, and with and without DC magnet systems. Alternately, the processing plasma in process space 12 can be formed using electron cyclotron resonance (ECR). In yet another embodiment, the processing plasma in process space 12 is formed from the launching of a Helicon wave. In yet another embodiment, the processing plasma in process space 12 is formed from a propagating surface wave.

A controller 26 includes a microprocessor, a memory, and a digital I/O port capable of generating control voltages sufficient to communicate and activate inputs to the processing system 1 as well as monitor outputs from the processing system 1. Moreover, the controller 26 is coupled to and can exchange information with the plasma processing chamber 10, the gas injection system 40, optical diagnostic sensor 22, and the vacuum pump system 38. For example, a program stored in the memory can be utilized to control the aforementioned components of a plasma processing system 1 according to a stored process recipe. One example of controller 26 is a DELL PRECISION WORKSTATION610™, available from Dell Corporation, Dallas, Tex.

Various system components can contain emitters that are capable of producing characteristic fluorescent light emission to indicate material buildup on system components in the presence of a plasma. The system components can include, but are not limited to, focus ring 60 containing emitter 28, shield 14 containing emitter 32, and electrode plate 24 containing emitter 34. These exemplary system components are consumable parts that, during plasma processing, commonly become coated, eroded, or both, and therefore require monitoring to facilitate proper replacing.

The role of focus ring 60 that encircles the substrate 35, includes control of the substrate etch rate, etch selectivity, and etch uniformity on the periphery of the substrate 35. The status (extent of erosion or material deposition) of focus ring 60 is commonly determined ex-situ by removing the focus ring 60 from the plasma processing system 1 and measuring the reduction or increase in the thickness of the focus ring 60. Alternatively, the status of the focus ring can be evaluated by visual inspection. For example, a change in order of few tenths of a mm in the thickness of the focus ring 60, can require replacement of the focus ring 60.

During manufacturing of various system components, emitters may be integrated into the system component structures to allow monitoring of component status. The preferred location of the emitters can be determined from process history and process requirements. When materials deposit on the emitters during plasma processing, reduced fluorescent emission from the emitters can result and can require cleaning or replacing of system components.

Various consumable or replaceable components of a plasma processing system are, for example, fabricated from silicon, quartz, alumina, carbon, or silicon carbide. Examples of consumable system components that are fabricated from these materials include electrodes, shields, rings, baffles, and liners. The consumable nature of the replaceable components can require frequent maintenance of the plasma processing system. In addition to the above-mentioned materials, system components (e.g., deposition shields) can be fabricated from metals (e.g., aluminum) and metal alloys (e.g., stainless steel) and require frequent cleaning or replacing.

Various materials (e.g., quartz and alumina) that are used to manufacture system components are substantially transparent to plasma light over a wide range of wavelengths. Fluorescent emission can be observed from emitters in these materials, even though the emitters are not in direct contact (e.g., encapsulated by the system component material) with the plasma environment. The amount of material deposited onto a system component can, for example, be determined when the fluorescent light emission falls below a threshold value.

Monitoring material deposition on a system component using an optical monitoring system can include determining if the intensity level of the fluorescent emission associated with a system component falls below a threshold value, arriving at a determination of whether the system component needs to be replaced, and based on the determination, either continuing with the process or stopping the process.

When the emitters are excited by a plasma, plasma light is absorbed and subsequently re-emitted as fluorescent light, that is shifted to longer wavelengths than the absorbed plasma light. The absorbed plasma light can, for example, be in the UV region and the emitted fluorescent light can be in the visible region. The shift to longer wavelengths can be advantageous, since light in the visible region is less affected by contaminants, such as polymers and by-products, that can deposit on the optical window 17 of the optical monitoring system 21 during processing. Exposure of the emitters to energetic species, other than light, in the plasma (e.g., excited gas species), can also result in fluorescent light emission.

The emitters can be selected from a wide variety of materials (e.g., fluorescent materials, that are commercially available in the form of rigid or non-rigid sheets, fine powders, or paints, for example). The emitters can be isolated parts or layers and the outer surfaces of system components can be partially or fully coated by the fluorescent materials. The emitters can contain at least one material having fluorescent properties corresponding to a light wavelength produced in a plasma. The fluorescent materials can be selected in view of the desired fluorescent properties that can depend on the plasma species, and the plasma chemistry. The selection of a fluorescent material may be evaluated in view of possible contamination of the process environment, due to exposure of the fluorescent material to the plasma, and possible erosion of fluorescent material from system components.

Phosphors compounds are examples of fluorescent materials that are frequently used in display applications. Phosphors are capable of emitting light in the visible and/or ultraviolet spectrums upon excitation of the material by an external energy source such as a plasma. Phosphor powders can have well-controlled color characteristics, sometimes referred to as emission spectrum characteristics or chromaticity. Phosphors typically include a matrix compound, referred to as a host material, and one or more dopants, referred to as activator ions, to emit a specific color or to enhance the luminescence characteristics. The phosphor materials (the color of the fluorescent light in parentheses), can include $Y_2O_3$:Eu (red), $Y_2O_2S$:Eu, Tb or combinations thereof (red), thiogallates (e.g., $SrGa_2S_4$:Eu (green)), ZnS:Cu, Al or combinations thereof (green), $SrGa_2S_4$:Ce (blue), ZnS:Ag, Au or Cl or combinations thereof (blue), and $SrGa_2S_4$:Ce (blue). The above-identified phosphors are exemplary; a wide variety of other phosphors can be utilized.

Figure 2B:
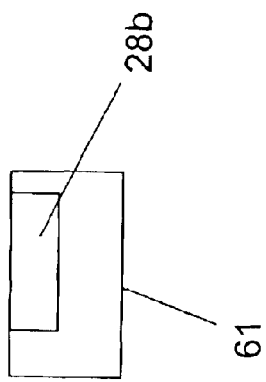
FIG. 2B shows a cross-sectional view of the system component in FIG. 2A.
Figure 2C:
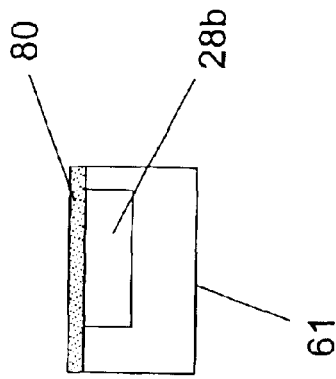
FIG. 2C shows a cross-sectional view of the system component in FIG. 2A with a layer of deposited material.
Figure 2A:
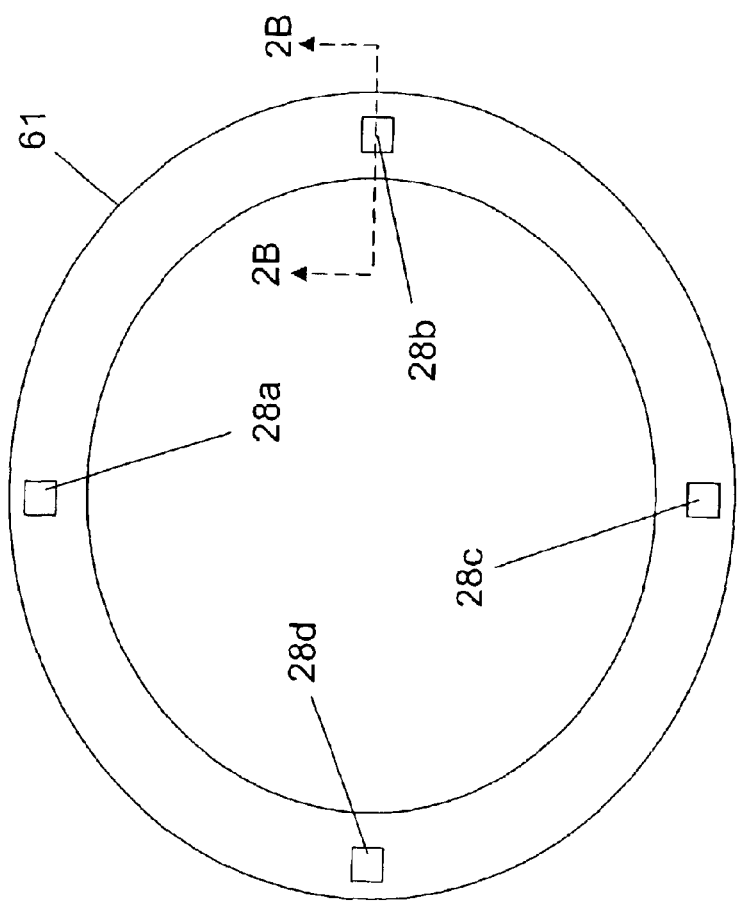
FIG. 2A shows a plan view of a system component containing a plurality of emitters.

FIG. 2A shows a plan view of a system component containing a plurality of emitters. In the exemplary embodiment shown in FIG. 2A, the system component is a ring 61. The ring 61 can, for example, be a focus ring, an insulator ring, or a shield ring. Emitters 28a–28d, capable of emitting fluorescent light when exposed to a plasma, are integrated into the ring 61. The number of emitters shown in FIG. 2A is exemplary; any number of emitters can be utilized. The emitters 28a–28d can contain at least one fluorescent material. The emitters can contain different fluorescent materials, or alternatively, the emitters can contain the same fluorescent material(s). Although the emitters 28a–28d are shown as squares in the embodiment in FIG. 2A, this is not required for the invention, In alternate embodiments, the emitters can have different shapes including non-geometrical and geometrical shapes, such as, for example, rectangular, circular, elliptical, and triangular shapes. FIG. 2B shows a cross-sectional view of the system component in FIG. 2A. The emitter 28b is partially encapsulated by the ring material (e.g., quartz, alumina, or silicon). Alternatively, at least one of the emitters 28a–28c can be fully encapsulated by the ring material. Although the cross-sectional shape of emitter 28b is shown as a rectangle in the embodiment in FIG. 2B, this is not required for the invention, In alternate embodiments, the emitter's cross-section can have different shapes including non-geometrical and/or geometrical shapes (e.g., as discussed above with reference to FIG. 2A).

FIG. 2C shows a cross-sectional view of the system component in FIG. 2A with a layer of deposited material. The system component 61 in FIG. 2C contains a layer 80 of deposited material that can be deposited during plasma processing. The layer 80 can, for example, consist of polymer deposits from plasma etching processes or metal deposits from plasma deposition processes. Optical monitoring of the process space 12, and disappearance of or significant decrease in characteristic fluorescent light emission from at least one of emitters 28a–28c below a threshold value, can be utilized to determine whether the system component needs to be cleaned or replaced.

Figure 3B:
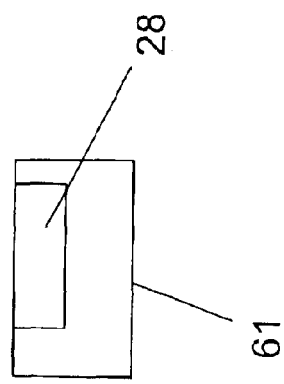
FIG. 3B shows a cross-sectional view of the system component in FIG. 3A.
Figure 3C:
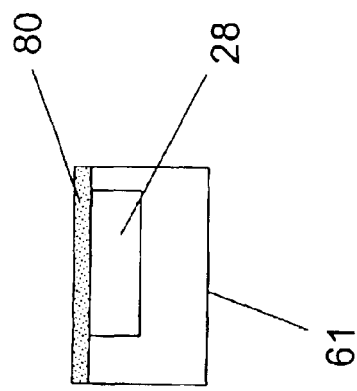
FIG. 3C shows a cross-sectional view of the system component in FIG. 3A with a layer of deposited material.
Figure 3A:
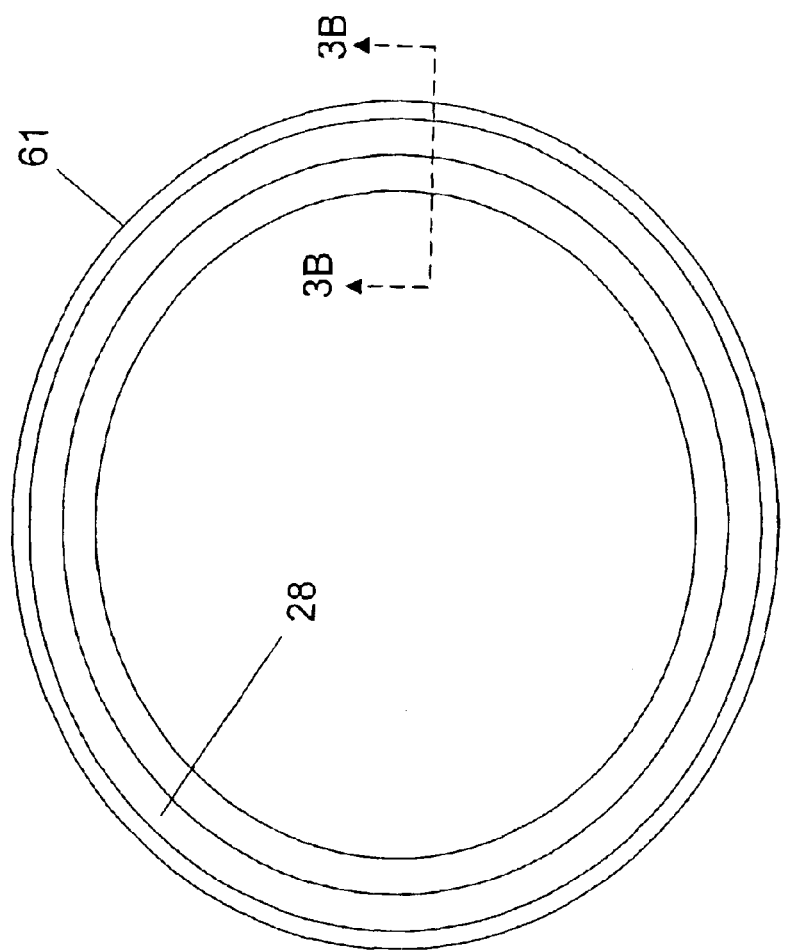
FIG. 3A shows a plan view of a system component containing an emitter.

FIG. 3A shows a plan view of a system component containing an emitter. In the embodiment shown in FIG. 3A, the system component is a ring 61. The emitter 28 is ring shaped and is partially encapsulated by ring material. Alternatively, the emitter can be fully encapsulated by the ring material. The emitter 28 can contain one or more fluorescent materials. FIG. 3B shows a cross-sectional view of the system component in FIG. 3A. In one embodiment, the ring shaped emitter uses a different emitter type (e.g., a different fluorescent material) in each quadrant so that buildup in each quadrant can be monitored. Smaller divisions (e.g., eighths or sixteenths) can also be used.

FIG. 3C shows a cross-sectional view of the system component from FIG. 3A with a layer of deposited material. The system component 61 in FIG. 3C contains a layer 80 deposited during plasma processing. Optical monitoring of the process space 12, and disappearance of or significant decrease in characteristic fluorescent light emission from emitter 28 below a threshold value, can be utilized to determine whether the system component needs to be cleaned or replaced.

FIG. 4A shows a plan view of a system component containing a plurality of emitters. In the embodiment shown in FIG. 4A, the system component is a ring 61. Emitters 28a–28c, capable of emitting fluorescent light when exposed to a plasma, are integrated into the ring 61 at different radial positions and are partially encapsulated by the ring material. Alternatively, the emitters can be integrated into the ring 61 at the same radial positions. Alternatively, at least one of the emitters 28a–28c can be fully encapsulated by the ring material. The number of emitters shown in FIG. 4A is exemplary; any number of emitters can be utilized. The emitters 28a–28c can contain at least one fluorescent material. The emitters can contain different fluorescent materials, or alternatively, the emitters can contain the same fluorescent material(s). FIG. 4B shows a cross-sectional view of the system component in FIG. 4A. In one embodiment, by selecting different materials, or combinations of materials, the buildup in each quadrant can be monitored separately.

FIG. 4C shows a cross-sectional view of the system component from FIG. 4A with a layer of deposited material. The ring 61 in FIG. 4C contains a layer 80 deposited during plasma processing. Optical monitoring of the process space 12, and disappearance of or significant decrease in characteristic fluorescent light emission from one or more of the emitters 28a–28c below a threshold value, can be utilized to determine whether the system component needs to be cleaned or replaced.

If the ring 61 becomes uniformly coated by layer 80, fluorescent light emission from exposed emitters 28a–28c can disappear substantially at the same time. However, if the layer 80 is non-uniformly (not shown) deposited during plasma processing, the characteristic fluorescent light emission from one or more of emitters 28a–28c can provide spatial deposition information, in addition to the extent of deposition on the ring 61.

Figure 5B:
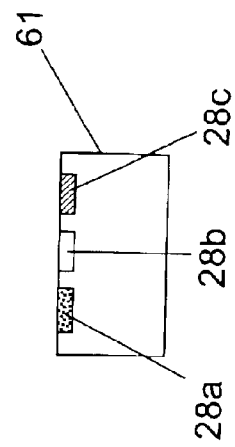
FIG. 5B shows a cross-sectional view of the system component in FIG. 5A.
Figure 5C:
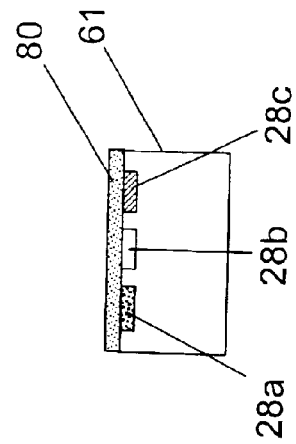
FIG. 5C shows a cross-sectional view of the system component in FIG. 5A with a layer of deposited material.
Figure 5A:
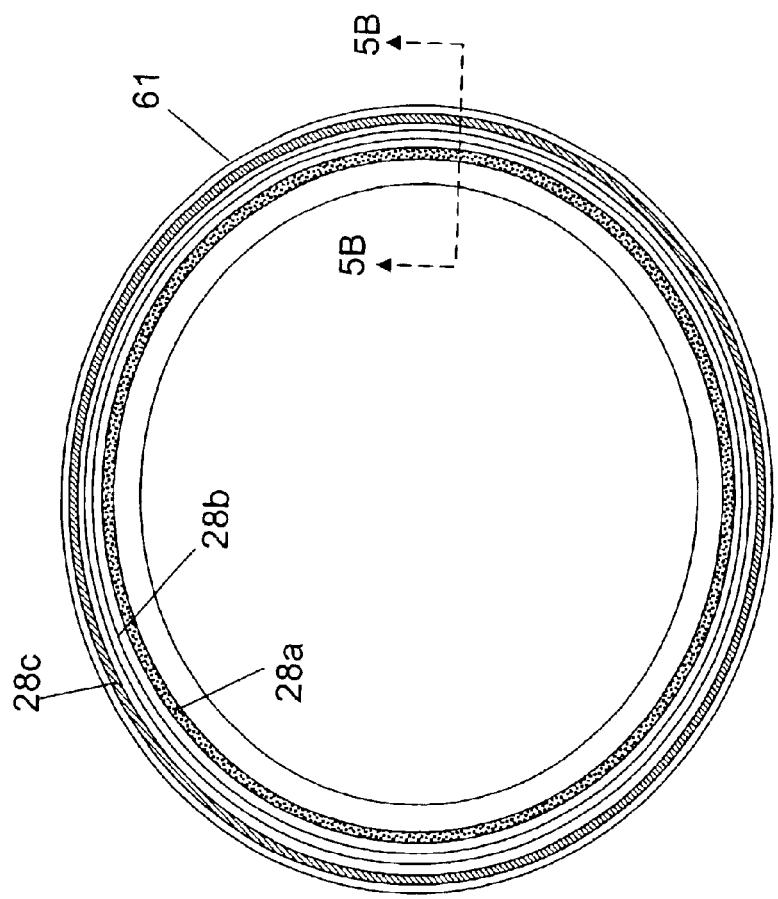
FIG. 5A shows a plan view of a system component containing a plurality of emitters.

FIG. 5A shows a plan view of a system component containing a plurality of emitters. In the embodiment shown in FIG. 5A, the system component is a ring 61. Emitters 28a–28c, capable of emitting fluorescent light when exposed to a plasma, are integrated into the ring 61 as concentric rings at different radial positions and are partially encapsulated by the ring material. Alternatively, at least one of the emitters 28a–28c can be fully encapsulated by ring material. The number of emitters shown in FIG. 5A is exemplary; any number of emitters can be utilized. The emitters 28a–28c can contain at least one fluorescent material. The emitters can contain different fluorescent materials, or alternatively, the emitters can contain the same fluorescent material(s). FIG. 5B shows a cross-sectional view of the system component in FIG. 5A. Spatial distribution of emitters 28a, 28b, and 28c can be used to measure non-uniform deposition on the system component. In one embodiment, the material within any one ring changes from quadrant to quadrant or between some other sized regions (e.g., eighths or sixteenths).

FIG. 5C shows a cross-sectional view of the system component from FIG. 5A with a layer of deposited material. The system component 60 in FIG. 5C contains a layer 80 deposited during plasma processing. Optical monitoring of the process space 12, and disappearance of or significant decrease in characteristic fluorescent light emission from one or more of the emitters 28a–28c below a threshold value, can be utilized to determine whether the system component needs to be cleaned or replaced.

Figure 6B:
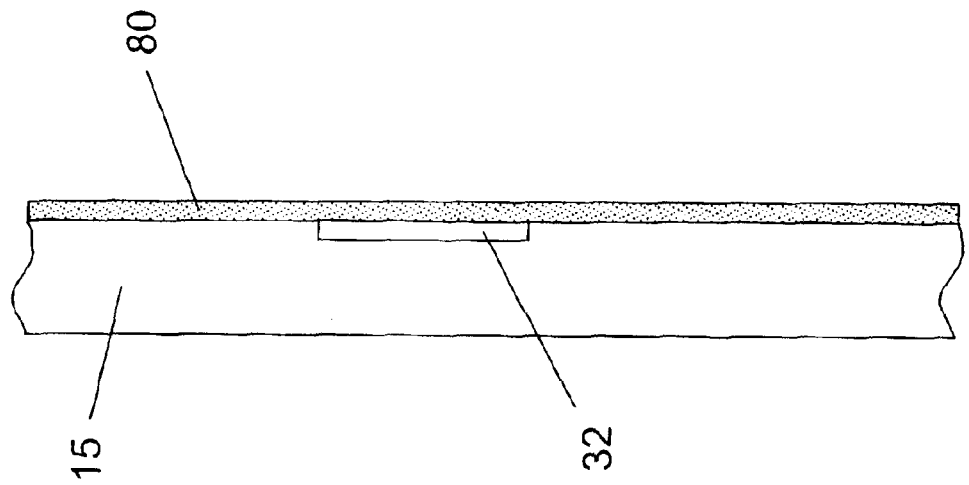
FIG. 6B shows a cross-sectional view of the system component in FIG. 6A with a layer of deposited material.
Figure 6A:
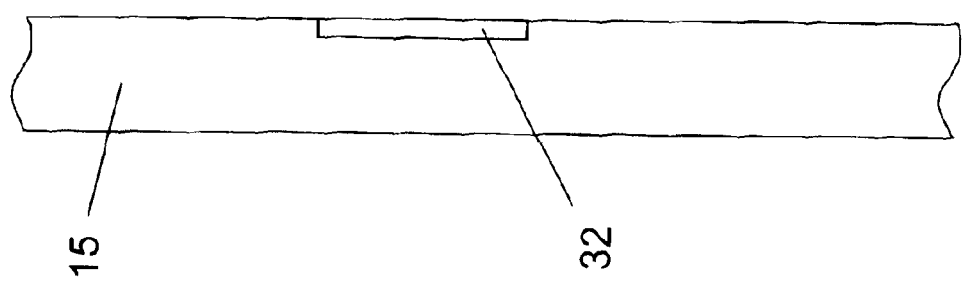
FIG. 6A shows a plan view of a system component containing an emitter.

FIG. 6A shows a cross-sectional view of a system component containing an emitter. In the embodiment shown in FIG. 6A, the system component 15 can, for example, be a ring, a shield, an electrode, a baffle, or a liner. In one embodiment, the system component 15 is a deposition shield that reduces deposition of material on chamber walls during plasma processing. An emitter 32, containing at least one fluorescent material and capable of emitting fluorescent light when exposed to a plasma, is integrated into the system component 15. The emitter 32 is partially encapsulated by the system component material (e.g., quartz, alumina, or aluminum). Alternatively, the emitter can be fully encapsulated within the system component 15.

FIG. 6B shows a cross-sectional view of a plasma processed system component from FIG. 6A with a layer of deposited material. During plasma processing, the system component 15 can be exposed to the plasma environment and this can result in deposition of layer 80 onto the system component 15. Alternately, during plasma processing, a chamber wall can be exposed to the plasma environment and this can result in deposition of layer 80 onto the chamber wall. Optical monitoring of the plasma processing system, and the disappearance of or significant decrease in characteristic fluorescent light emission from emitter 32 below a threshold value, can be utilized to determine whether the system component needs to be cleaned or replaced.

Figure 7C:
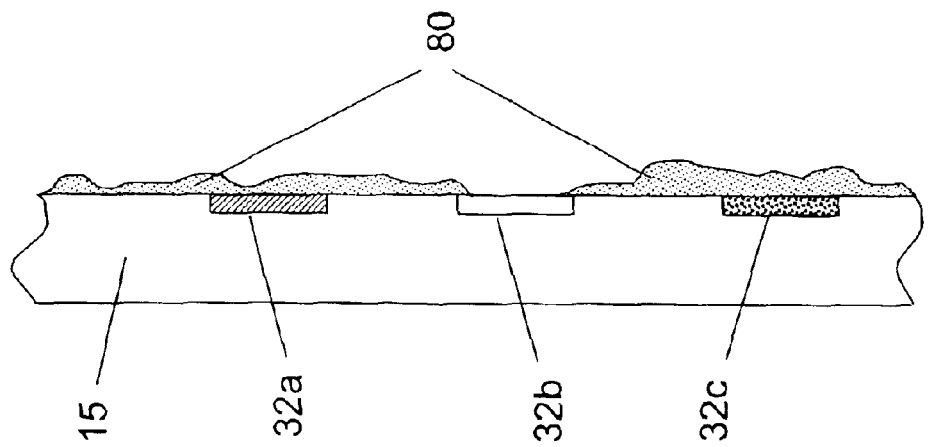
FIG. 7C shows a cross-sectional view of the system component in FIG. 7A with a layer of deposited material.
Figure 7B:
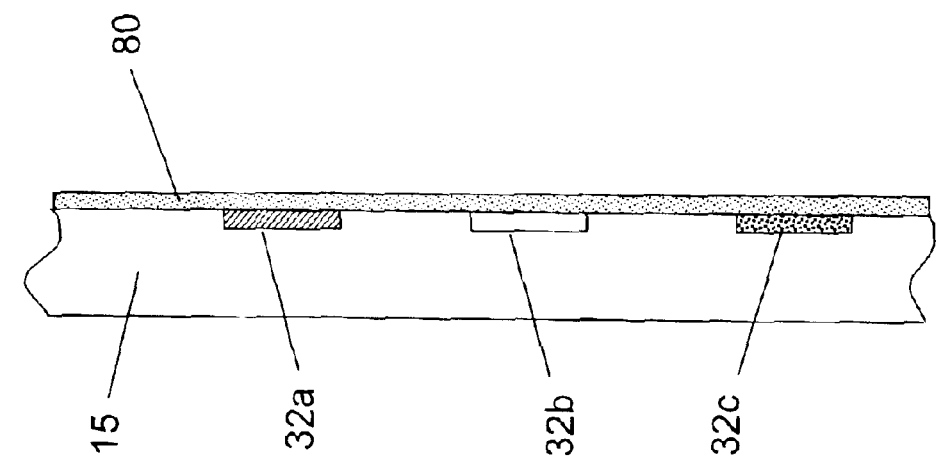
FIG. 7B shows a cross-sectional view of the system component in FIG. 7A with a layer of deposited material.
Figure 7A:
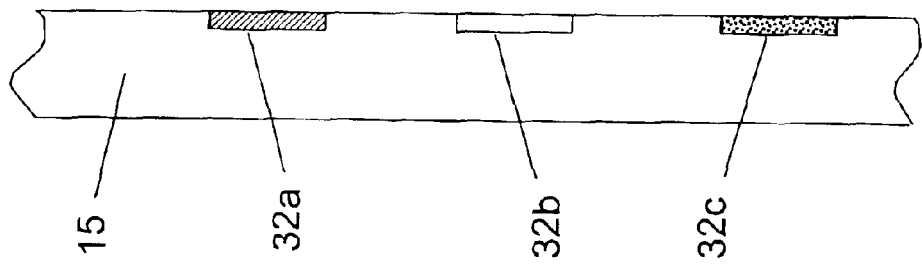
FIG. 7A shows a cross-sectional view of a system component containing a plurality of emitters.

FIG. 7A shows a cross-sectional view of a system component containing a plurality of emitters. In FIG. 7A, the emitters 32a–32c are partially encapsulated by the ring material. Alternatively, the emitters can be fully encapsulated by the ring material.

FIG. 7B shows a cross-sectional view of the system component in FIG. 7A with a layer of deposited material. The system component is uniformly coated, and fluorescent signals from emitters 32a–32c can appear substantially at the same time. FIG. 7C shows a cross-sectional view of the system component in FIG. 7A with a layer of deposited material. In FIG. 7C the system component 15 is non-uniformly coated by layer 80, and the characteristic fluorescent light emission from one or more of emitters 32a–32c can provide spatial deposition information, in addition to information on the extent of the deposition on the system component 15.

Different system components in a plasma processing system can contain different fluorescent materials that allow identifying and monitoring a particular system component. In addition, a single system component can contain different fluorescent materials at different spatial locations to allow monitoring of material buildup on multiple sites on the system component. System components can contain protective barriers that are deposited on the surfaces of the system components. The role of a protective barrier can be to reduce erosion of the system components during plasma processing. A protective barrier comprising, for example Yttria ($Y_2O_3$), can be formed using (thermal) spray coating techniques that are well known to those skilled in the art of ceramic spray coatings. In an alternate embodiment, forming the protective barrier can further comprise polishing the thermal spray coating. For example, polishing the thermal spray coating can comprise the application of sand paper to the sprayed surfaces. The protective barrier can comprise at least one of $Y_2O_3$, $Sc_2O_3$, $Sc_2F_3$, $YF_3$, $La_2O_3$, $CeO_2$, $Eu_2O_3$, $DyO_3$, $SiO_2$, $MgO$, $Al_2O_3$, $ZnO$, $SnO_2$, and $In_2O_3$. The protective barrier thickness can range from 0.5 microns to 500 microns, for example. Alternatively, the protective barrier can comprise a phosphor material, e.g. $Y_2O_3$:Eu. Disappearance of a characteristic fluorescent light emission from a phosphor material in a protective barrier can be used to determine deposition on a system component.

Figure 8B:
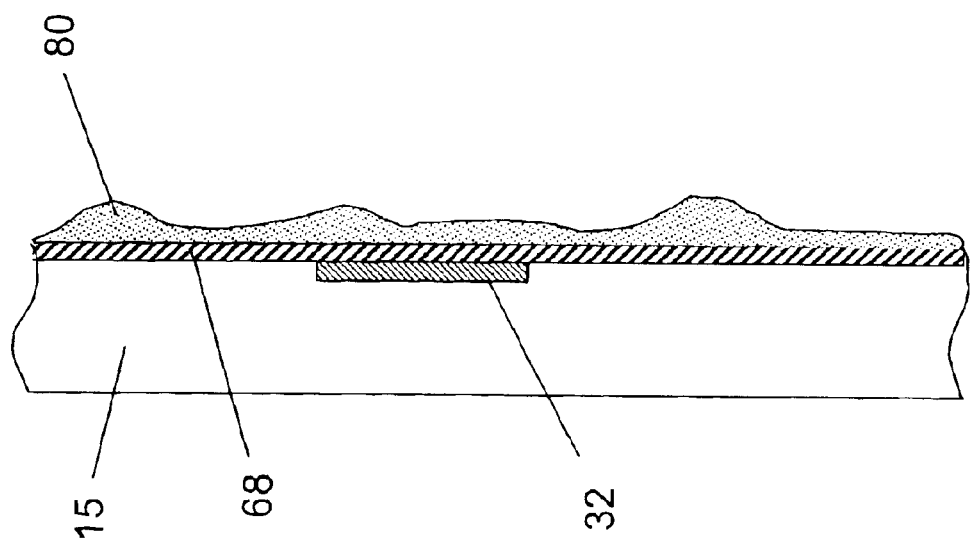
FIG. 8B shows a cross-sectional view of the system component in FIG. 8A with a layer of deposited material.
Figure 8A:
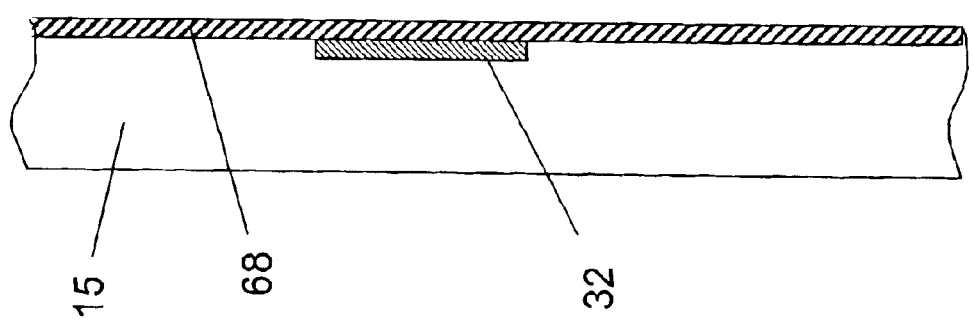
FIG. 8A shows a cross-sectional view of a system component containing an emitter and a protective layer.

FIGS. 8A and 8B show a cross-sectional view of a system component containing an emitter. FIG. 8A shows a protective barrier layer 68 deposited on the emitter 32 and system component 15. FIG. 8B shows a layer 80 deposited on the system component. Changes in the fluorescent emissions from emitter 32 during plasma processing can indicate deposition on the protective barrier layer 68.

FIGS. 9A and 9B show a cross-sectional view of a system component containing an emitter. FIG. 9A shows an emitter overlying a protective barrier layer 68 deposited on system component 15. FIG. 9B shows a non-uniform layer 80 deposited on the system component. Changes in the fluorescent emissions from emitter 32 during plasma processing can indicate deposition on the protective barrier layer 68.

FIGS. 10A and 10B show a cross-sectional view of a system component containing an emitter. FIG. 10A shows an emitter layer overlying a protective barrier layer 68 deposited on system component 15. FIG. 10B shows a non-uniform layer 80 deposited on the system component. Changes in the fluorescent emissions from emitter 32 during plasma processing can indicate deposition on the emitter layer 32.

Deposition of material on a system component can be determined during plasma processing, by monitoring the characteristic fluorescent emission from an emitter integrated into the system component. One possible method for determining the status of a system component is to use optical emission spectroscopy (OES) to monitor a wavelength range where the characteristic fluorescent emission occurs. A system component can contain at least one emitter, that is capable of fluorescent emission at characteristic wavelength(s), that allows for identification of the system component. When an intensity level of an emission with a characteristic wavelength crosses a specified threshold value (e.g., increase above a particular value or drop to substantially zero), a determination can be made whether the system component needs to be cleaned or replaced, and based on the determination, the process can be continued or stopped.

Figure 11:
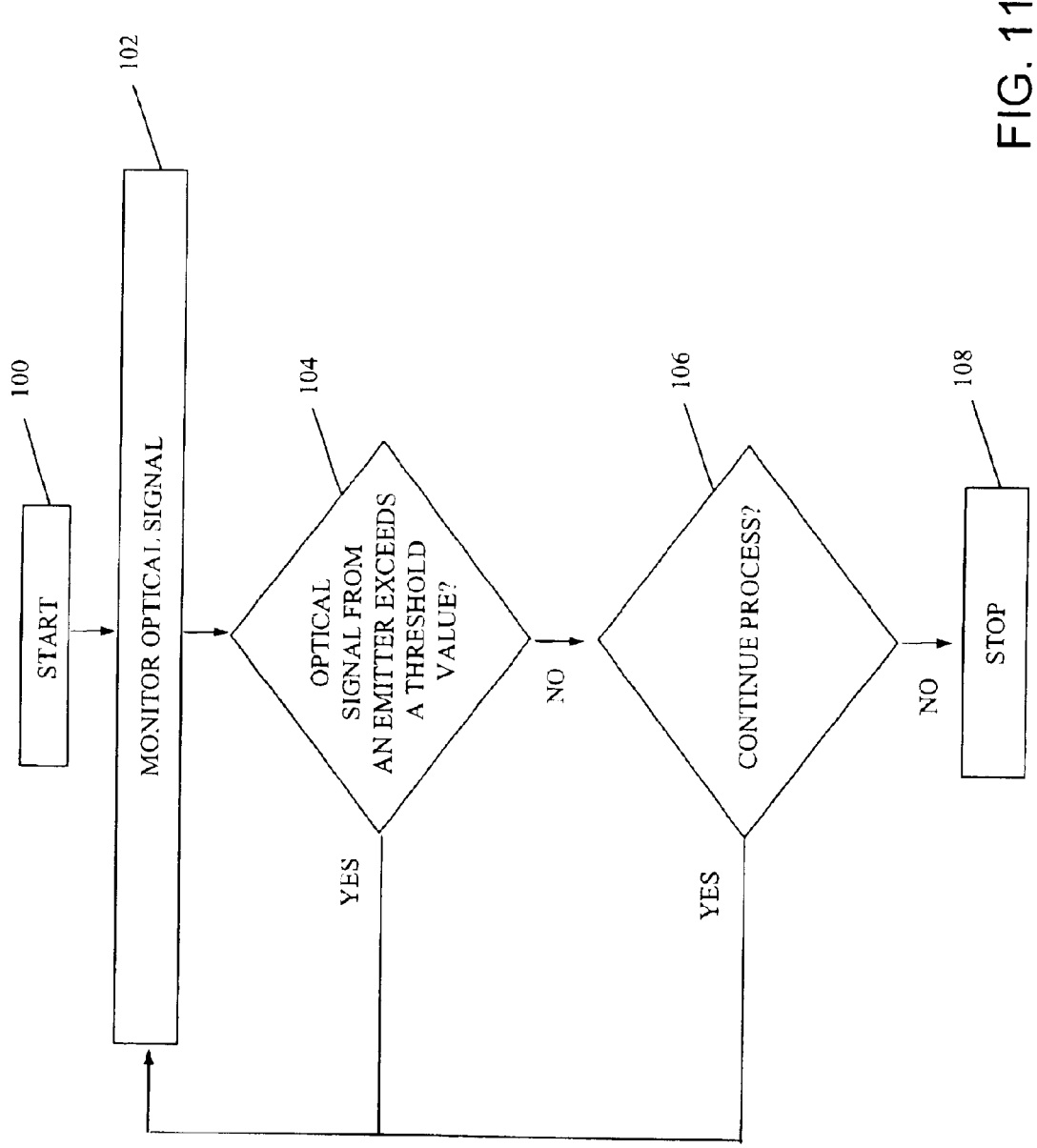
FIG. 11 is a flowchart for monitoring the status of system components using optical emission.

FIG. 11 is a flowchart for monitoring the status of system components using optical emission. In step 100, the process is started. In step 102, an optical signal from the plasma processing region is monitored using an optical monitoring system. In step 104, the optical signal is analyzed for characteristic light emission from an emitter integrated into a system component. If the characteristic light emission from an emitter falls below a threshold value, a determination is made in step 106 on whether to continue the process or to stop the process in step 108.

Determining whether the process should be continued in step 106 can depend on the fluorescent emission that is detected, e.g., identifying the system component. Furthermore, fluorescent emission from a plurality of emitters integrated into a system component can indicate if the system component is uniformly coated during plasma processing and can therefore provide spatial deposition information, in addition to the extent of the deposition.

This method of monitoring the status of system components using emitters, provides a new in-situ method for monitoring material buildup on system components in a plasma environment. The deposition of material onto consumable system components can be monitored during plasma processing, without the need for disassembly of the plasma processing system. The method can significantly reduce the risk of overdue or premature replacement of consumable components, and avoid processing conditions that are outside process specifications due to deposition of materials onto system components.

In an alternate embodiment (not shown), a transparent or translucent material is provided over the material to protect the emitter from damage (e.g., cause by exposure to the plasma). Such a material may either pass all wavelengths or may filter out a subset of the light from the plasma and/or from the emitter.

It should be understood that various modifications and variations of the present invention may be employed in practicing the invention. It is therefore to be understood that, within the scope of the appended claims, the invention may be practiced otherwise than as specifically described herein.

What is claimed is:

1. A method of monitoring material buildup on a system component in a plasma processing system, the method comprising:

exposing a system component to a plasma, the system component containing an emitter capable of fluorescent light emission when exposed to the plasma; and monitoring the fluorescent light emission from the plasma processing system during a process to determine buildup on the system component.

2. The method according to claim 1, wherein the fluorescent light emission relates to an amount of material buildup on the system component.

3. The method according to claim 1, wherein the system component comprises a consumable part.

4. The method according to claim 1, wherein the system component comprises at least one of a ring, a shield, an electrode, a baffle, and a liner.

5. The method according to claim 1, wherein the emitter comprises at least one material having fluorescent properties when excited by a light produced in the plasma.

6. The method according to claim 1, wherein the emitter comprises at least one material having fluorescent properties when excited by excited gas species produced in the plasma.

7. The method according to claim 1, wherein the monitoring comprises using an optical monitoring system to detect the fluorescent light emission.

8. The method according to claim 7, wherein the monitoring comprises determining if the intensity level of the fluorescent emission falls below a threshold value.

9. The method according to claim 7, wherein the monitoring further comprises identifying the system component from the wavelength of the fluorescent light emission.

10. The method according to claim 7, wherein the monitoring further comprises measuring an intensity level of the fluorescent emission to arrive at a determination of whether the component needs to be cleaned or replaced, and based on the determination, either continuing with the process or stopping the process.

11. A method of monitoring material buildup on a system component in a plasma processing system, the method comprising:

exposing a system component to a plasma, the system component containing an emitter capable of fluorescent light emission when exposed to the plasma; and monitoring fluorescent light emission from the plasma processing system during a process, the monitoring including using an optical monitoring system to detect the wavelength and the intensity level of the fluorescent light emission, identifying the system component from the wavelength of the fluorescent light emission, and arriving at a determination of the status of material buildup on the system component.

12. A plasma processing system, comprising:

a plasma processing chamber;

a plasma source configured to create a plasma from a process gas;

a system component containing an emitter capable of fluorescent light emission when exposed to a plasma;

an optical monitoring system for monitoring light emission from the plasma processing chamber during processing to monitor status of material buildup on the system component; and a controller configured to control the plasma processing system.

13. The system according to claim 12, wherein the system component comprises a consumable part.

14. The system according to claim 12, wherein the system component comprises at least one of a ring, a shield, an electrode, a baffle, and a liner.

15. The system according to claim 12 wherein the system component is fabricated from least one of silicon, quartz, alumina, carbon, silicon carbide, aluminum, and stainless steel.

16. The system according to claim 12 wherein the emitter comprises at least one material having fluorescent properties when excited by light produced in a plasma.

17. The system according to claim 12, wherein the emitter comprises at least one material having fluorescent properties when excited by excited gas species produced in the plasma.

18. The system according to claim 17, wherein the at least one material comprises a phosphor material.

19. The system according to claim 18, wherein the phosphor material comprises at least one of $Y_2O_3$:Eu, $Y_2O_2$S:Eu, $Y_2O_2$S:Tb, $Y_2O_2$S:EuTb, ZnS:Cu, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl, and $SrGa_2S_4$:Ce.

20. The system according to claim 12, wherein the system component further comprises a protective barrier.

21. The system according to claim 20, wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

22. The system according to claim 20, wherein the protective barrier is transparent.

23. The system according to claim 12, wherein a cross-section of the emitter in the depth direction is non-constant.

24. The system according to claim 12, wherein the plasma source comprises an inductive coil.

25. The system according to claim 12, wherein the plasma source comprises a plate electrode.

26. The system according to claim 12, wherein the plasma source comprises an ECR source.

27. The system according to claim 12, wherein the plasma source comprises a Helicon wave source.

28. The system according to claim 12, wherein the plasma source comprises a surface wave source.

29. A plasma processing system, comprising:

a plasma processing chamber;

a plasma source configured to create a plasma from a process gas;

a system component containing an emitter capable of fluorescent light emission when exposed to a plasma;

an optical monitoring system for monitoring light emission from the plasma processing chamber during processing to monitor status of material buildup on the system component; wherein the optical monitoring system is further configured to identify the system component from the wavelength of the fluorescent light emission, to determine if the intensity level of the fluorescent emission exceeds a threshold value, to determine if the system component needs to be replaced, and based on the determination, either continue with the process or stop the process; and a controller configured to control the plasma processing system.

30. A monitorable consumable system component, comprising:

an annular element; and an emitter coupled to the annular element, the emitter being capable of fluorescent light emission during a plasma process, wherein the light emission is used to monitor status of material buildup on the system component.

31. The consumable system component according to claim 30, wherein the annular element comprises a ring, a shield, an electrode, a baffle, or a liner.

32. The consumable system component according to claim 30, wherein the annular element is a focus ring.

33. The consumable system component according to claim 30, wherein the annular element is an electrode plate.

34. The consumable system component according to claim 30, wherein the annular element is a deposition shield.

35. The consumable system component according to claim 30, wherein the annular element is fabricated from least one of silicon, quartz, alumina, carbon, silicon carbide, aluminum, and stainless steel.

36. The consumable system component according to claim 30, wherein the emitter is fully encapsulated by the annular element.

37. The consumable system component according to claim 30, wherein the emitter is partially encapsulated by the annular element.

38. The consumable system component according to claim 30, wherein the emitter comprises at least one material having fluorescent properties when excited by light produced in a plasma.

39. The consumable system component according to claim 30, wherein the emitter comprises at least one material having fluorescent properties when excited by excited gas species produced in a plasma.

40. The consumable system component according to claim 30, wherein the light emission from the emitter allows for identifying the consumable system component.

41. The consumable system component according to claim 30, wherein the emitter comprises a phosphor material.

42. The consumable system component according to claim 41, wherein the phosphor material comprises at least one of $Y_2O_3$:Eu, $Y_2O_2S$:Eu, $Y_2O_2S$:Tb, $Y_2O_2S$:EuTb, ZnS:Cu, ZnS:Al, ZnS:CuAl, $SrGa_2S_4$:Ce, ZnS:Ag, ZnS:Au, ZnS:Cl, ZnS:AgAu, ZnS:AgCl, ZnS:AuCl, ZnS:AgAuCl, and $SrGa_2S_4$:Ce.

43. The consumable system component according to claim 30, wherein the system component further comprises a protective barrier.

44. The consumable system component according to claim 43, wherein the protective barrier comprises at least one of $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

45. The consumable system component according to claim 43, wherein the protective barrier comprises at least one material having fluorescent properties when excited by light produced in a plasma.

46. The consumable system component according to claim 43, wherein the protective barrier comprises at least one material having fluorescent properties when excited by excited gas species produced in a plasma.

47. The consumable system component according to claim 43, wherein a thickness of the protective barrier is less than about 500 microns.

* * * * *